United States Patent [19]

Betzold et al.

[11] Patent Number: 5,658,320

[45] Date of Patent: Aug. 19, 1997

[54] ATRIAL TACHYARRHYTHMIA DETECTION IN IMPLANTABLE PULSE GENERATORS

[75] Inventors: Robert A. Betzold, Fridley; David E. Dalluge, Plymouth, both of Minn.

[73] Assignee: Medtronic, Inc., Mpls., Minn.

[21] Appl. No.: 536,713

[22] Filed: Sep. 29, 1995

[51] Int. Cl.$^6$ ................................................ A61N 1/362
[52] U.S. Cl. ................................................ 607/14; 128/705
[58] Field of Search .............................. 607/9, 14, 697, 607/705

[56] References Cited

U.S. PATENT DOCUMENTS

| | | |
|---|---|---|
| 4,363,325 | 12/1982 | Roline . |
| 4,374,382 | 2/1983 | Markowitz . |
| 4,556,063 | 12/1985 | Thompson . |
| 4,562,841 | 1/1986 | Brockway . |
| 4,587,970 | 5/1986 | Holley . |
| 4,802,483 | 2/1989 | Lindgren ................ 607/14 |
| 4,856,523 | 8/1989 | Sholder . |
| 4,856,524 | 8/1989 | Baker . |
| 5,052,388 | 10/1991 | Sivula . |
| 5,103,820 | 4/1992 | Markowitz ................ 607/9 |
| 5,127,404 | 7/1992 | Wyborny . |
| 5,144,949 | 9/1992 | Olson . |
| 5,271,395 | 12/1993 | Wahlstrand . |
| 5,273,035 | 12/1993 | Markowitz et al. ........... 607/14 |
| 5,274,491 | 12/1993 | Sutton . |
| 5,342,405 | 8/1994 | Duncan ................ 607/14 |

OTHER PUBLICATIONS

Provenier et al., The "Automatic Mode Switch" Function in Successive Generations of Minute Ventilation Sensing Dual Chamber Rate Responsive Pacemakers, in Pace, vol. 17, Nov. 1994, Part II, pp. 1913–1919.

Ovsyshcher et al., "Initial Experience with a New Algorithm for Automatic Mode Switching From DDDR to DDIR Mode", PACE, vol. 17, Nov. 1994, Part II, 1908–12.

Levine, et al., A New Automode Switch Algorithm for Supraventricular Tachycardias, in PACE, vol. 17, Nov. 1991, Part II, pp. 1895–1899.

den Dulk et al., Initial Experience with Mode Switching in a Dual Sensor, Dual Chamber Pacemaker in Patients with Paroxysmal Atrial Tachyarrhythmias, in Pace, vol. 17, Nov. 1994, Part II, pp. 1990–1907.

*Primary Examiner*—Jeffrey R. Jastrzab
*Attorney, Agent, or Firm*—Michael B. Atlass; Harold R. Patton

[57] ABSTRACT

Because a determination of atrial tachycardia can occur too often where the pacemaker maintained true atrial interval value is designed to converge on the shortest A-A intervals, a method and apparatus either extends PVAB to cover inappropriate atrial senses that should not be counted in determining the true atrial interval, primarily where they occur after an atrial pace, or removes other AS events from consideration.

11 Claims, 5 Drawing Sheets

METHOD 3: IF SEQUENCE IS AR-AP AND MAI WAS DECREMENTED ON LAST UPDATE, THEN ADD CORRECTION FACTOR TO MAI

METHOD 1: DYNAMIC BLANKING AS OR AP

FIG. 7a

METHOD 2: IF SEQUENCE IS AP-AR, SKIP MAI UPDATE

FIG. 8

ATRIAL TACHYARRHYTHMIA DETECTION IN IMPLANTABLE PULSE GENERATORS

BACKGROUND OF THE INVENTION

In general, this invention relates to implantable pulse generators used to deliver stimulation to pace a patient's heart and particularly to those which detect atrial tachycardia and switch to either an antitachy pacing mode or a fallback mode on discovering indications of atrial tachycardia or atrial tachyarrhythmias.

In response to such indications, a pacemaker may perform in a number of different ways and it is not the purpose of this invention to detail such responses. Rather this invention is designed to prevent or reduce false responses. The usual response to tachy detection of current generation pacing devices is mode switching.

One method of responding to indications of tachycardia generally ignores the high intrinsic atrial rates and switches to ventricular pacing as described in U.S. Pat. No. 5,144,949 (Olson). This is a type of mode switching. Other systems use alternative operations in antitachy mode such as that described in U.S. Pat. No. 4,587,970 (Holley et at.) which uses reversion pacing to try to disrupt and discontinue the tachycardia. A fairly detailed background on pacemaker technology for mode switching is found in U.S. Pat. No. 4,562,841 (Brockway et at.).

Mode switching has had various definations and purposes in the pacemaker or pacing and pulse generator art. Examples, besides those mentioned above, include U.S. Pat. Nos. 5,284,491 (Sutton et at.), U.S. Pat. No. 4,856,523 (Sholder et al.), and U.S. Pat. No. 4,363,325 (Roline et at.). These use a sensor rate or some long term or changing atrial rate to determine when mode switching is to be done for the particular problems that those patents address. In general they are inventions responsive to problems developed because of or during rate adaptive pacing. Mode switching can best be described as where the pacemaker reverts to a mode that does not track (i.e., does not pace the ventricle in synchronization to) the atrial rate. Another way to say this is that in a mode switched condition pacing does not synchronize ventricular pacing to intrinsic atrial activity. Methods and features of mode switching are described in the Nov. 19, 1994 (Vol. 17, Part II) issue of PACE magazine in the article titled "A New Automode Switch Algorithm for Supraventricular Tachycardias" by Levine et al on pp. 1895–9. (Additional articles on automatic mode switching devices were also published in the same issue of PACE at pages 1900 (Den Dulk), 1908 (Ovsyshcher) and 1913 (Proverder).

Rate adaptive pacers which follow a patient's physiologic demand have been available for some time. A recent example is illustrated in U.S. Pat. No. 5,271,395 (Wahlstrand et at.). U.S. Pat. No. 4,856,524 (Baker, Jr.) uses an AV interval timer instead of an activity sensor (as in U.S. Pat. No. 5,052,388 to Sivula et at.) or minute ventilation (as in U.S. Pat. No. 5,271,395 Wahlstrand) to determine the appropriate pacing rate.

When mode switching is used however, certain timing sequences have been known to cause false positive indicators. That is the problem specifically addressed by this invention.

Pacemaker technology has been around for some 30 years. The technology for implanting such hermetically sealed electrical pulse generators (usually with batteries for power) responsive to a patient's pacing needs are well known in many aspects and those will not be described with particularity here. Instead, the reader should refer to descriptions available in the art cited in this application and other available literature.

In responding to this problem of false positive tachy indicators, the implantable pulse generator had been pacing at or near the programmed lower rate before, during, and after the erroneous indicator caused a pacemaker response. Commonly that response was referred to as a mode switch episode. These episode durations were generally short (less than one minute) but could be much longer. The AP-V-AR and AP-AR-V timing sequences (where the AP-AR interval is short relative to the size of the long interval AR-AP) sustained over multiple pacing cycles were generally felt responsible for false positive tachy detection and thus causing these inappropriate mode switch episodes. (Definitions: AP means atrial pace, V means ventricular event, AR means atrial refractory sense). Because a pacemaker senses these events through intracardiac electrical lead(s), it is mainly thought that these patterns can be the result of far field R-wave sensing or possibly from sensing retrograde P-waves. Test results using marker channel information (as described in U.S. Pat. No. 4,374,382 issued to Markowitz et al.) are available which show such occurrences as we have been describing. In general, a marker channel diagram is one indication of pacemaker interpretation of sensed cardiac or similar seeming noise events.

Our algorithms employ a timing variable which for convenience may be called the mean atrial interval (or MAI or Average Atrial Interval AAI) and represents what the pacing device or "pacemaker" considers the true atrial interval. Our AAI is also designed to converge on the shortest A-A interval (when long-short interval patterns are occurring). In certain situations this AAI/MAI algorithm can converge on the short AP-AR interval (described above) and thus identify such sequences as atrial tachycardia even in the absence of actual atrial tachycardia. This invention's algorithms can apply to any pacemaker that has false detection of tachycardia or atrial flutter, but one preferred embodiment is found in its application to the MAI in the Thera (TM) Medtronic pacemaker.

Other adjustments can also be made in the modem pacemaker which are described in reference to alternate preferred embodiments herein.

SUMMARY OF THE INVENTION

Alternate methods are described to prevent false positive responses to non-existent atrial tachycardia or flutter. An object of this invention is thus to avoid potential indicators of tachy detection from causing inappropriate pacemaker responses. One simple way is to avoid using any indication of atrial tachycardia during atrial pacing. A preferred embodiment lengthens or shortens PVAB to accomplish this. Other features allow for not only avoiding events in determining whether there is tachycardia, but for filtering out event sequences such as AP-AR-VS sequences.

To avoid atrial tracking, the monitoring algorithm screens or filters sensed heart activity for pacing pulses. It can thereby avoid AP-AR intervals by ignoring them or adapting to them in various ways or instead by adjusting the Post Ventricular Atrial Blanking (PVAB) period to avoid sensing the AR event altogether.

The pacemaker algorithm can check for the presence of atrial tracking or atrial pacing to determine if a mode switch is appropriate. Atrial tracking is defined by the presence of AS-VP sequences, i.e., the ventricle is paced to follow the atrial event. Atrial pacing involves AP-V sequences whereby the atrium is paced and the ventricle responds by natural conduction through the AV node from the paced atrium or is paced by the pacemaker. A simplified logic suggests that one should not mode switch if there is atrial pacing at all. (It should be remembered that being in a dual chamber pacing mode does not always mean pacing in both chambers. An AP event is not generally triggered in dual pacing mode if there is a natural sinus(atrial) rhythm. Thus, the assumption is that when there is an AP event, the natural sinus rate is insufficient i.e., not tachy.)

Two methods and their combination are discussed. First, the internal variable that values the A-A interval can be adjusted beat-by-beat to filter-out or correct for certain unwanted AP-AR intervals. Or second, the length of post ventricular atrial blanking (PVAB) can be modulated so that it is longer after atrial paced events and shorter after atrial sensed events. The longer blanking would prevent sensing an AR event which follows an AP, thus preventing a mode switch during atrial pacing. Combining the first and second should prevent most false tachy detection.

DETAILED DESCRIPTION OF PREFERRED EMBODIMENTS

First a description of the pacemaker system follows.

Figure 2:
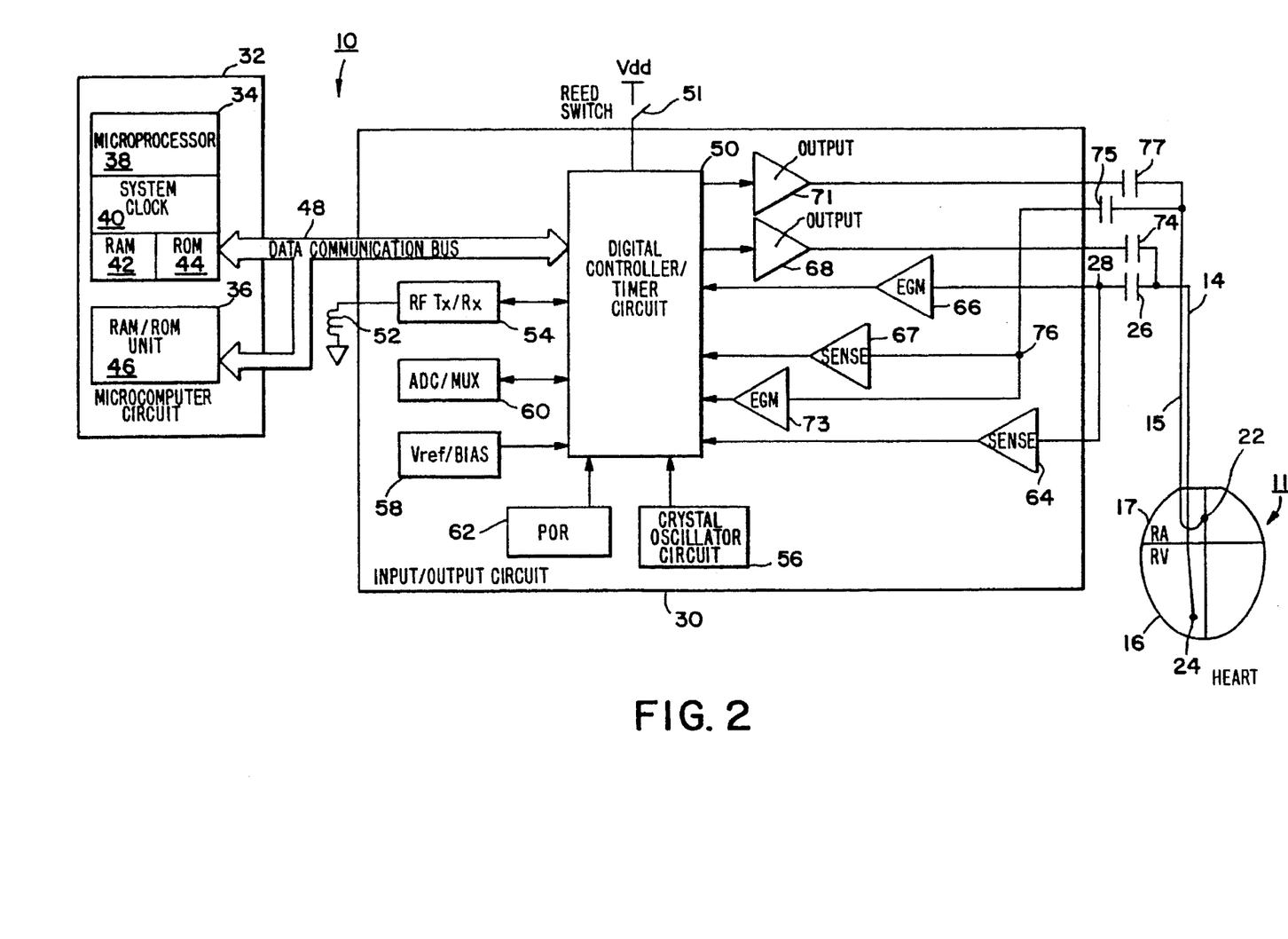
FIG. 2 is a block diagram illustration of the component parts of a generalized pacemaker for use with this invention, also illustrating its connection to the heart..

FIG. 2 is a block circuit diagram illustrating one possible form of a pacemaker 10 capable of carrying out the present invention. Although the present invention is described in conjunction with a microprocessor-based architecture, it is understood that it could be implemented in other technology such as digital logic-based, custom integrated circuit (IC) architecture, analog circuits, etc., if desired. It is also understood that the present invention may be implemented in cardioverters, defibrillators and the like.

Preferred embodiments would use two leads, 14, 15. Lead 14 includes an electrode 24 located near its distal end positioned within the right ventricle 16. Electrode 24 is coupled by a lead conductor 14 through an input capacitor 26 to the node 28, and to the input/output terminals of an input/output circuit 30. Lead 15 has a distal electrode 22 positioned within the right atrium 17. Electrode 22 is coupled by a lead conductor 15 through an input capacitor 75 to a node 76, and to the input/output terminals of the input/output circuit 30.

Input/Output Circuit 30 contains the operating input and output analog circuits for digital controlling and timing circuits to detect electrical signals derived from the heart, such as the cardiac electrogram (EGM or ECG). It also receives output from sensors (not shown but which may be connected to the leads 14 and 15), and it is the part which applies stimulating pulses to the heart under the control of software-implemented algorithms in a Microcomputer Circuit 32.

Microcomputer Circuit 32 has an On-Board Circuit 34 and an Off-Board Circuit 36. On-Board Circuit 34 includes a microprocessor 38, a system clock 40, and on-board RAM 42 and ROM 44. Off-Board Circuit 36 includes an off-board RAM/ROM Unit 46. Microcomputer Circuit 32 is coupled by Data Communication Bus 48 to a Digital Controller/ Timer Circuit 50. Microcomputer Circuit 32 may be fabricated of custom IC devices augmented by standard RAM/ROM components.

It will be understood by those skilled in the art that the electrical components represented in FIG. 2 are powered by an appropriate implantable-grade battery power source (not shown).

An antenna 52 is connected to Input/Output Circuit 30 for purposes of uplink/downlink telemetry through a radio frequency (RF) Transmitter/Receiver Circuit (RF TX/RX) 54. Telemetering both analog and digital data between antenna 52 and an external device, such as an external programmer (not shown), is accomplished in the preferred embodiment by means as substantially described in U.S. Pat. No. 5,127, 404, issued on Jul. 7, 1992, entitled "Telemetry Format for Implantable Medical Device", incorporated herein by reference. A reed switch 51 is connected to Input/Output Circuit 30 to enable patient follow-up via disabling the sense amplifier 146 and enabling telemetry and programming functions, as is known in the art.

A Crystal Oscillator Circuit 56, typically a 32,768 Hz crystal-controlled oscillator, provides main timing clock signals to Digital Controller/Timer Circuit 50. Most timing periods depend on a clock to mm on or off under program control, and the length of timing is generally established with reference to a number of clock cycles. A Vref/Bias Circuit 58 generates a stable voltage reference and bias currents for the analog circuits of Input/Output Circuit 30. An ADC/Multiplexer Circuit (ADC/MUX) 60 digitizes analog signals and voltages to provide telemetry and a replacement time-indicating or end-of-life function (EOL). A Power-on-Reset Circuit (POR) 62 functions to initialize the pacemaker 10 with programmed values during power-up, and reset the program values to default states upon the detection of a low battery condition or transiently in the presence of certain undesirable conditions such as unacceptably high electromagnetic interference (EMI), for example.

The operating commands for controlling the timing of the pacemaker depicted in FIG. 2 are coupled by bus 48 to Digital Controller/Timer Circuit 50 wherein digital timers set the overall escape interval of the pacemaker, as well as various refractory, blanking and other timing windows for controlling the operation of the peripheral components within Input/Output Circuit 50. For this invention these are particularly the PVAB and MAI values.

Digital Controller/Timer Circuit 50 is coupled to sense amplifiers (SENSE) 64 and 67, and to electrogram (EGM) amplifiers 66 and 73 for receiving amplified and processed signals picked up from electrode 24 through lead 14 and capacitor 26, and for receiving amplified and processed signals picked up from electrode 22 through lead 15 and capacitor 75, representative of the electrical activity of the patient's ventricle 16 and atrium 17, respectively. Similarly, SENSE amplifiers 64 and 67 produce sense event signals for re-setting the escape interval timer within Circuit 50. The electrogram signal developed by EGM amplifier 66 is used in those occasions when the implanted device is being interrogated by the external programmer/transceiver (not shown) in order to transmit by uplink telemetry a representation of the analog electrogram of the patient's electrical heart activity as described in U.S. Pat. No. 4,556,063, issued to Thompson et at., entitled "Telemetry System for a Medical Device", incorporated herein by reference.

Output pulse generators 68 and 71 provide the pacing stimuli to the patient's heart 11 through output capacitors 74 and 77 and leads 14 and 15 in response to paced trigger signals developed by Digital Controller/Timer Circuit 50 each time the escape interval times out, or an externally transmitted pacing command has been received, or in response to other stored commands as is well known in the pacing art.

In a preferred embodiment of the present invention, pacemaker 10 is capable of operating in various non-rate-responsive modes which include DDD, DDI, VVI, VOO and VVT, as well as corresponding rate-responsive modes of DDDR, DDIR, VVIR, VOOR and VVTR. Further, pacemaker 10 can be programmably configured to operate such that it varies its rate only in response to one or more selected sensor outputs, if desired. Many other features and functions of pacemakers may be incorporated without going beyond the scope of this invention.

Some background information about marker channels and how pacemakers keep information regarding A-A intervals is also required.

Figure 1:
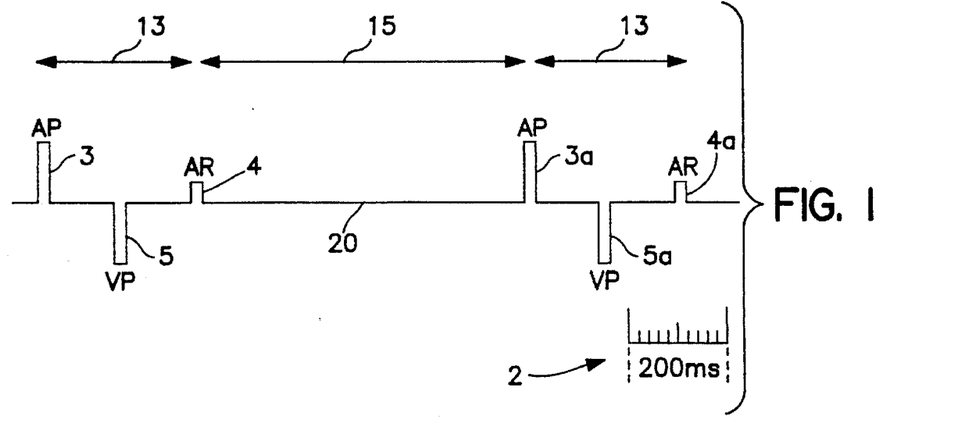
FIG. 1 is a marker channel diagram providing an example of a timing scenario which can cause false positive tachy detection and mode switching.

Referring now to FIG. 1, although a number of algorithms could be used to determine the average atrial interval, the ones we use tend toward convergence on the shortest atrial interval value in a repeating sequence. (This can be recognized by examining the AAI algorithm discussed below.) This convergence on the shortest time AA interval is how mode switching is generally triggered. (We assume this is the "true" A-A value and call this updated atrial interval value either the Average Atrial Interval (AAI) or Mean Atrial Interval (MAI) for convenience.) These A-A interval time values tend to be significantly shorter than atrial pace to atrial pace intervals as can be easily seen in FIG. 1. Here a marker channel diagram 20 is illustrated with atrial pace indicators 3/3a, atrial refractory event indicators 4/4a, and ventricular pace indicators 5/5a. The arrows 13 (for AP-AR intervals) and 15 (for AR-AP intervals) indicate the likely differences in timing between atrial to atrial events for this patient. For size reference, indicator scale 2 is included on the diagram of FIG. 1.

Figure 3:
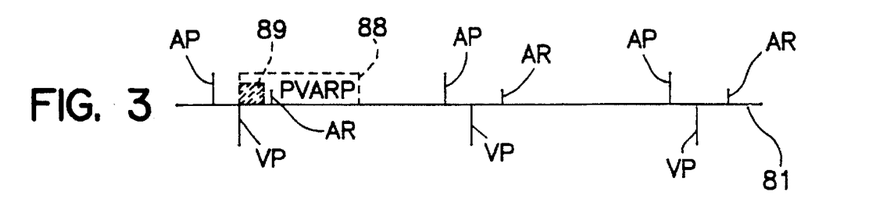
FIGS. 3–5 are marker channel diagrams.
Figure 4:
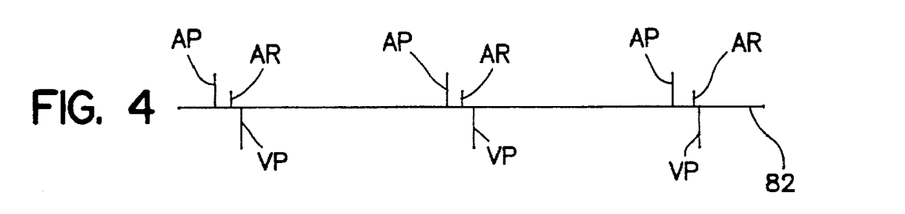

FIGS. 3 and 4 illustrate cases where false tachy detection could occur, as shown in these marker channel diagrams (illustrated as lines or graphs 81 and 82). The atrial pace, atrial refractory, and ventricular pace events are simply indicated with AP, AR, and VP, respectively. In FIG. 3 a sensed event in a post ventricular atrial refractory period (PVARP 88) (shown here as AR) may be due either to far field R-waves (FFRWs), T-wave sensing, retrograde conduction, skeletal muscle activity artifacts, or any other sense occurring during PVARP, or false atrial sensing due to polarization after a pacing pulse. (For heuristic purposes and reference a PVAB period 89 is also shown within the PVARP 88 in FIG. 3.) In a second case (FIG. 4), a sense during the Atrio Ventricular (AV) interval is shown. This may be due to ventricular fusion pacing, loss of atrial capture, junctional rhythm, or any other atrial sense during the AV interval which can fool the tachy detection algorithm by suggesting that the true atrial interval is very short.

Far field R-wave sensing may occur in cases other than an AP-AR-AP rhythm. It is also possible to get a far field R-wave after a sinus rhythm, producing an AS-VP-AR marker channel series. While in general it may be assumed that the marker channel diagram of FIG. 3 has appropriately labeled marker signals, these may be incorrect. For example, a far field R-wave or other signal may appear to be something other than it seems. If that is the case, the marker channel generator will label it incorrectly, indicating that the pacemaker may respond incorrectly.

In other pulse generators, there may be no marker channel reference but the device may nonetheless misinterpret signals. The marker channel is used in this description because it is much more easily read than strip charts and because it indicates how the pacemaker is interpreting the sensed signals it is receiving from the heart and its environment.

Valuation of the "AAI" or "MAI" (a variable stored and updated by the pacemaker)

The current value of what we may refer to as an Average Atrial Interval is normally adjusted by a microprocessor, like microprocessor 38 (in FIG. 2), under control of a software program running in a RAM/ROM area like unit 46. This is done continuously following atrial interval measurements between two sequentially occurring atrial events.

There are numerous ways to adjust the AAI/MAI. These fall into three categories. 1) Ignoring certain individual cardiac sense events that occur during blanking periods, 2) ignoring other individual events that do not qualify because of the type of signal or the timing of the signal received, and 3) a set of methods through manipulation of the algorithm itself used to determine and update MAI. While many functions of a pacemaker may be dependent upon the calculation used to evaluate such an MAI variable, its clearest indication is in determining whether or not there is a tachycardia present. In general, MAI=F(N), (that is, Mean Atrial Interval is a function of a variable N)., where N is a continuously updated value dependent on determination of atrial events and the timing between one atrial event and the next. If MAI is greater than a predetermined amount, a decision is taken that tachycardia is present.

Thus the value of MAI can be shifted by ignoring certain atrial events that occur generally too close to a previous event, are of too small an amplitude, or occur too long after a previous event. On the occurrence of a valid A to A event interval, the value of that time period between the occurrence of first event and the second event is used to increase or decrease the value of MAI. This can be done directly or indirectly and various algorithmic filters and limitations may be put on this additive or subtractive function as will occur to the reader of ordinary skill in these arts.

A primary concern of this patent is to find an appropriate a value for the A to A interval in order to make a judgment about whether or not a tachyarrhythmic event is occurring. For example, in a sinus tracking situation, where every atrial event is a sensed (intrinsic) event, each A-A interval would be used in adjusting the MAI. In a competitive pacing situation, where atrial pacing is closely coupled to intrinsic atrial activity, the Refractory Sense-Pace(AR-AP) interval should not be used as it may not actually reflect the underlying intrinsic atrial rate.

Depending on the sophistication of the pacemaker or implanted pulse generating device, the internal recordkeeping of the MAI may be maintained in several places and if desired several different values can be used, one for each particular purpose.

In the presently preferred embodiment, updating the MAI is a "biased delta" operation. Each adjustment modifies the MAI by a fixed mount. If the measured A-A interval used for an update of the MAI is smaller than or equal to the current MAI, the MAI is reduced by a fixed mount, called "DELTA- DEC". Likewise, if the A-A interval used for an update of the MAI is larger than the current MAI, the MAI is increased by a different fixed amount, "DELTAINC". DELTADEC and DELTAINC are included among the programmable values. Such values could be selected and modified or manipulated by a physician, but in the preferred embodiment they are not programmable by a user. (Such a change of values, if desired, could be accomplished using the pulse generator's telemetry programming facilities, to modify certain memory locations in the device. Such telemetry and communication is a well-known practice in the art.)

For any given update, the MAI used in the preferred embodiment can never change by more than the DELTA-DEC or DELTAINC values. In the presently preferred implementation of the invention, DELTADEC is larger than DELTAINC. This results in a rate-smoothing pattern that tracks rapidly increasing atrial rates faster than decreasing atrial rates.

One result of the step-wise incrementing and decrementing of the MAI is that it is possible for the MAI to overshoot the intrinsic atrial rate. For example, if it is assumed (1) that a current MAI value is 600-mSec (milliseconds); (2) that the programmed DELTADEC value is 24-mSec; (3) that the programmed DELTAINC value is 8-mSec; (3) that an atrial sense occurs 550-mSec following a prior atrial sense (i.e., a measured atrial interval of 550-mSec). Then this will result in an updated MAI value of 576-mSec (600-24). If (4), the next intrinsic atrial event occurs 560-mSec following the one for which the MAI was updated to 576-mSec, the next MAI update would again entail decrementing the current MAI by 24-mSec. This adjustment, however, would result in an MAI of 552, slightly smaller than the intrinsic A-A interval (560-mSec) just measured. If the next intrinsic atrial event is in 560-mSec from the last one, DELTAINC will be added to 552 yielding a new MAI of 560-mSec.

Adjusting the AAI/MAI to Exclude Certain Sequences

Figure 5:
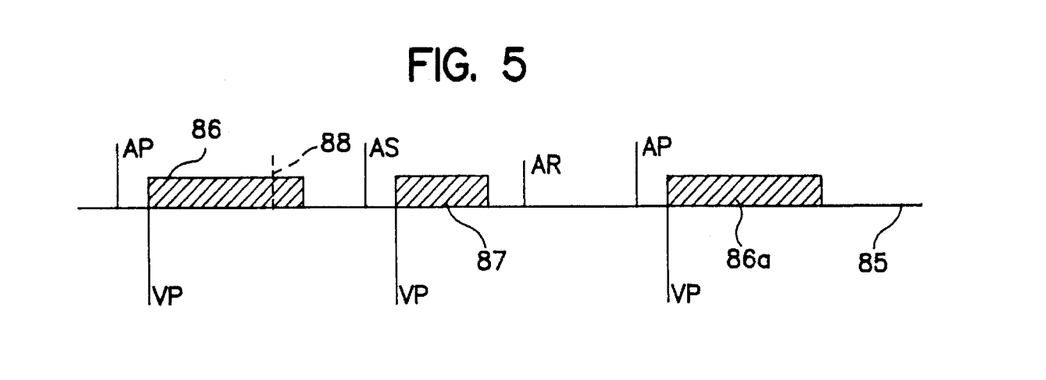

FIG. 5 is a marker channel diagram 85, illustrating three PVAB's (post ventricular atrial blanking periods) as numerals 86 and 87 and also illustrating a blanked atrial refractory sense 88. Starting at the left, the AP-AR (blanked at 88)-AS sequence is interpreted as an A-A interval measured from AP to AS, since AR, the Far Field R-Wave(FFRW)-type signal at 88 is ignored. Thus, in the case of a long PVAB (Post Ventricular Atrial Blanking period) like PVAB 86, the next marker channel atrial event is further out and this long A-A interval is used to update the MAI. Where the PVAB is shortened because it occurs after an atrial sense (not a paced) event as in PVAB 87, the AR or FFRW event is the next considered event by the tachy detection algorithm. In other words, the AS-AR interval will shorten the MAI/AAI (because it's a short time period), and if short enough the MAI size will indicate a tachy condition, and cause a mode switch. In this way the AAI/MAI is automatically adjusted by the changed length of the PVAB. In a preferred embodiment there are two possible PVAB lengths, one near 200 msecs and the short one around 150 msecs, although the reader may choose other values. These values could be adjusted by a physician if desired. Further, they may be automatically fine tuned (that is, increased or decreased in size by the pacemaker) based on a patient-pacemaker history that detects tachy events too frequently or too infrequently. A PVARP(Post Ventricular Atrial Refractory Period) may be used instead of (or including a) PVAB if either the sense amplifier is turned off during PVARP or that even if there is a (shorter) Blanking period (PVAB) within PVARP, that the AS will be ignored if in PVARP.

An alternative or second method is to adjust MAI or AAI to ignore AP-AR periods. Thus, a sequence AP-AP would "count" in figuring the updated MAI, as would AS-AS, but no reevaluation of MAI would occur if an AA interval is measured starting with an AP and ending with an AR event. This can be illustrated with reference to FIG. 4 in which the AR events occur before the Ventricular events. In such a case, no matter what length PVAB were used (because PVAB extends rightward from the VP event), the AR events would be considered in evaluating the MAI values if extending the PVAB were the only method to deal with these improper tachy indicator signals. In FIG. 4, then, the AP-AR interval would produce a short MAI and a false tachy indication. However, by returning the MAI value to its state before the AP-AR sequence occurred, (for example, by adding back in the DELTADEC that was subtracted), whenever an AP-AR sequence is encountered, the MAI will not converge on these false indicators, even when located in the temporal position as shown in FIG. 4. An alternative is to not update the MAI until at least a certain time has passed without finding AP-AR sequences, or to not update it until the next atrial event is recorded after a ventricular event and in either event leaving out the recognition of an interval between any AP's and AR's within such time.

Combining this first and second method provides a reasonable approach to eliminating improper pacemaker response to non-extant tachy events. If the improper signal is an AR after an AP it can be hidden in an extended PVAB, if it is an AR sense in the AV interval or beyond PVAB, it can be ignored or removed from the A-A interval update process, thus leaving the MAI at a true atrial interval value.

A third and closely related to the second method is to simply ignore any interval starting with an AP event.

These strategies are diagramatically represented in flow charts 101, 102, 103, and 104, of FIGS. 7a–d, respectively. In each, they start with an initiation step 105a–d, in which initial parameter values are set, and simply passed on after that. Also in each algorithmic process, the next step is to wait for the next atrial event and determine whether it is an atrial pace or sense event (106a, b, and d) or for an atrial paced event only 106c. In the first method 101, and in the combination method 104, a long PVAB 107 is produced following the next ventricular event if an AP was found and a short PVAB 108 if an atrial sense was found. Method 101 then proceeds to block 111a that is called upon to refigure the MAI or true atrial interval. In method 104, the MAI in all events is updated unless the last event from step 110d was an AP and the current event is AR. In that situation (AP-AR), the MAI is not updated (step 112d). The second method 102 refigures the MAI in block 111b or skips it in 112b, depending on whether the last atrial event was an AR following an AP or not (block 106b). The third method only operates after APs. In block 106c this is determined. If it was not AP, block 111c recalculates the true atrial interval. If it was AP, block 109 determines whether the last atrial event was an AR. If not, the MAI is updated in block 111c. If not another check is made in step 110, to see if the MAI was decremented the last time an atrial event went through process 103. If so, it adds back in that value, otherwise it simply updates the MAI through step 111c.

This updating of the MAI is preferably done as set forth above in the description of the MAI/AAI in the presently most preferred embodiment but one of ordinary skill in the art can easily apply these concepts to other pacemakers using merely similar algorithms without leaving the ambit of this invention.

Figure 6A:
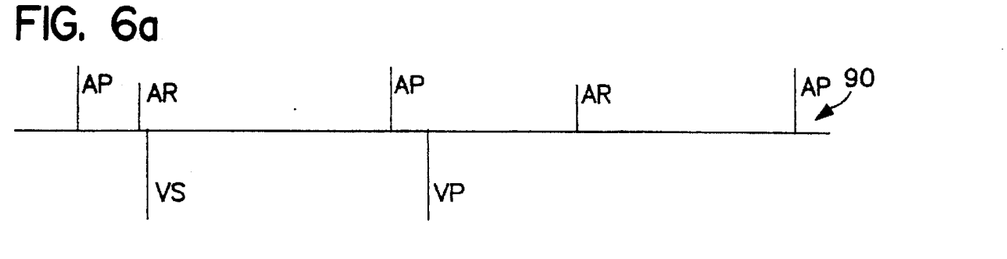
FIGS. 6a and 6b are graphs representing coincident timing between an electrocardiogram strip and a marker channel.
Figure 6B:
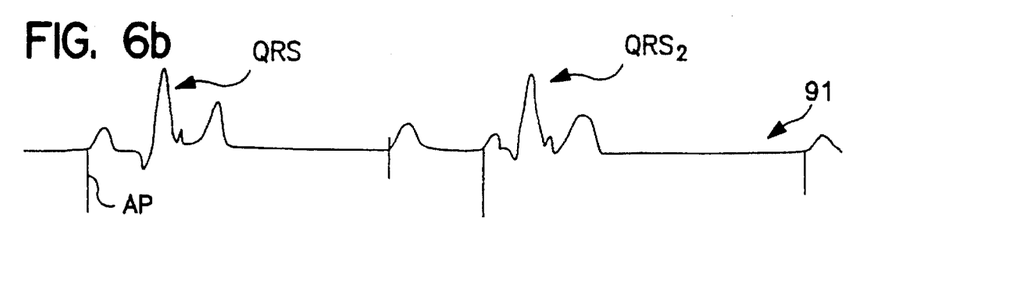
Figure 7A:
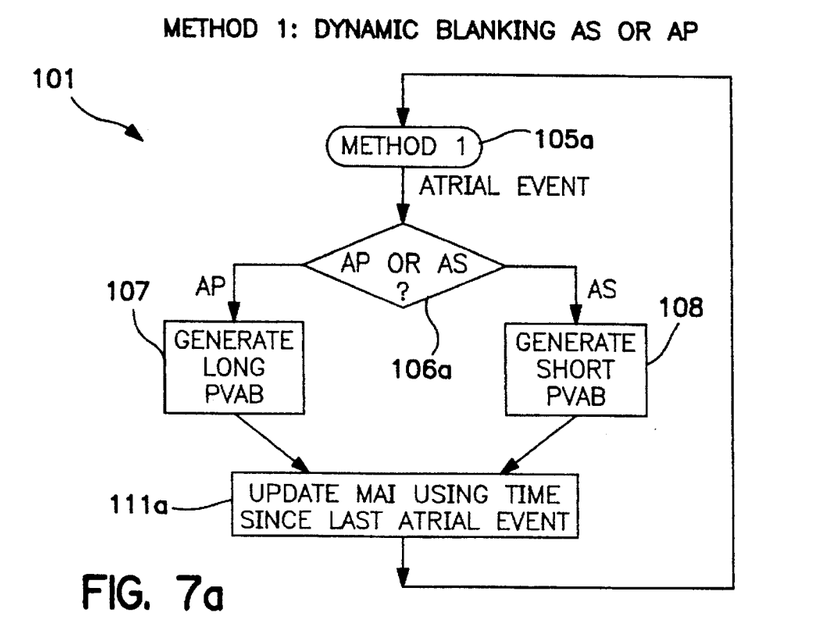
FIGS. 7a–7d are flow diagrams of algorithmic processes in accord with preferred embodiments of this invention.
Figure 7B:
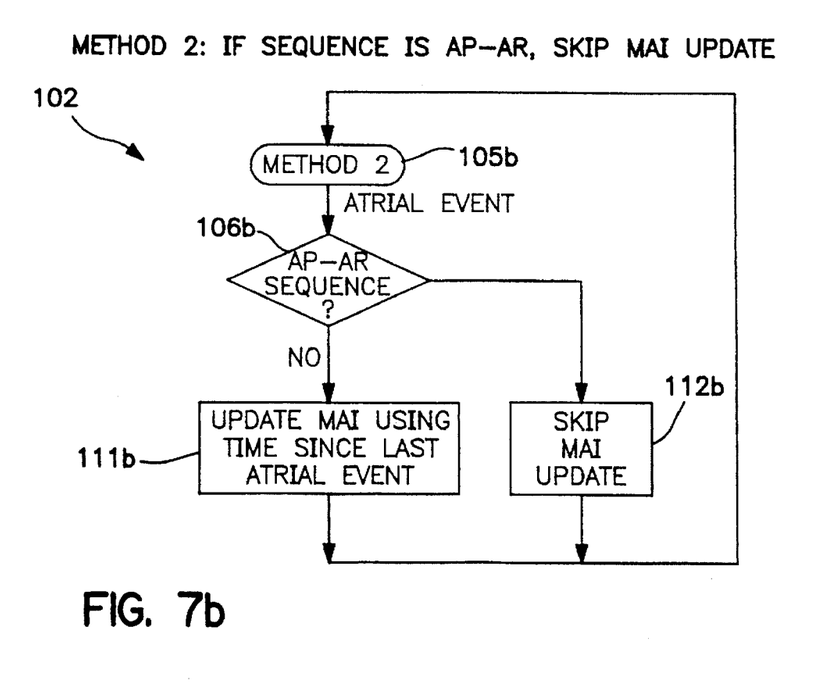
Figure 7C:
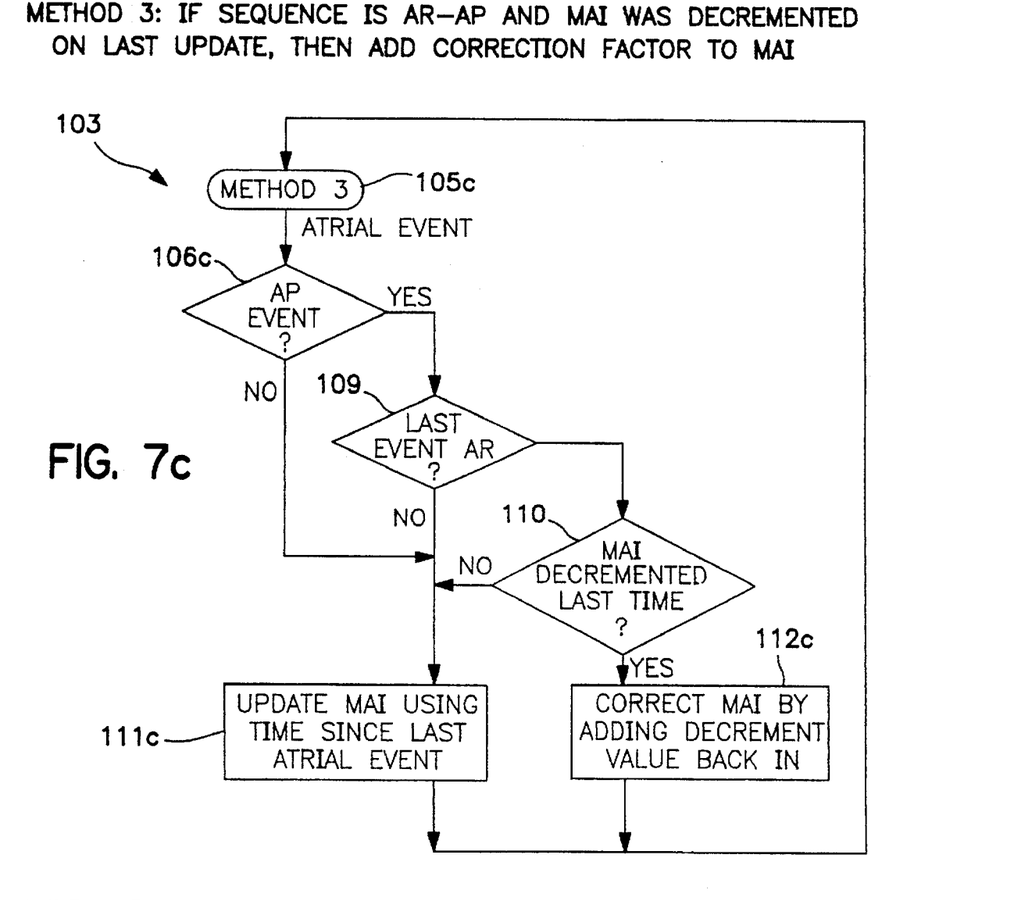
Figure 7D:
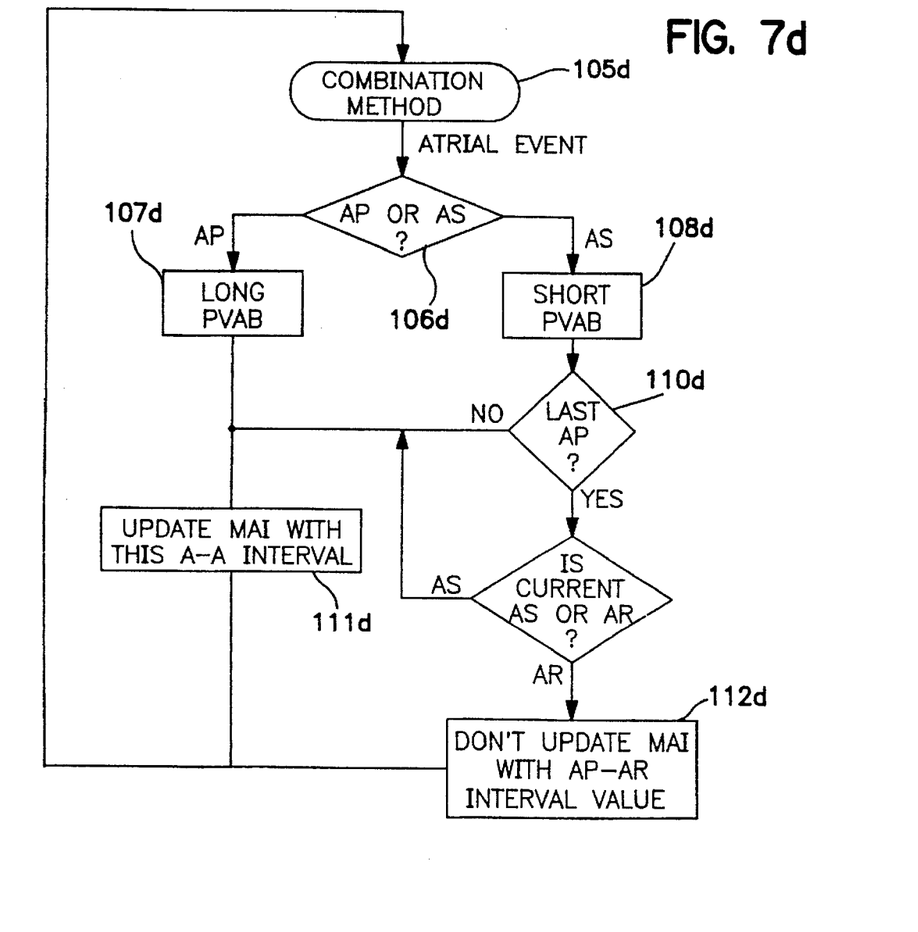
Figure 8:
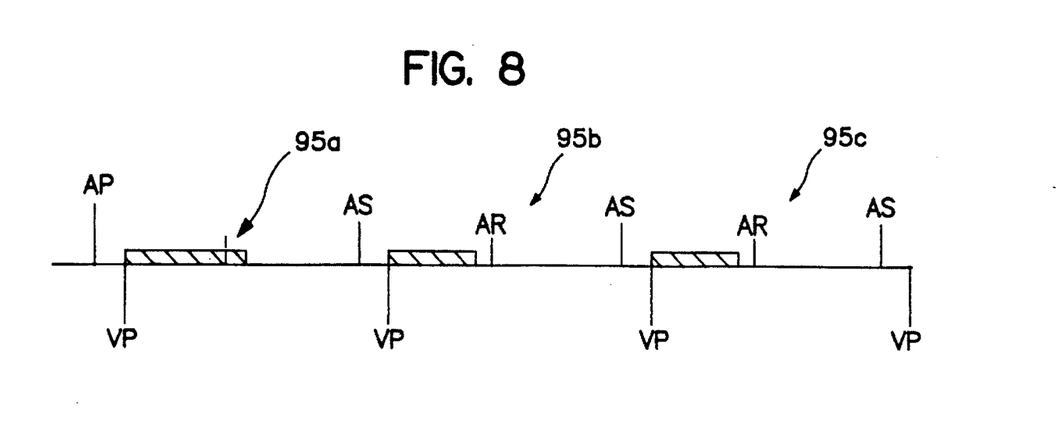
FIG. 8 is another marker channel diagram.

FIGS. 6a and b illustrate the timing correspondence between a marker channel 90 and an ECG 91 with false atrial sensed events AR. The first method can be used to filter out the false AR event in the AP-AR-V sequence on the left. While the second method can be used to filter out the false AR event in the AP-V-AR sequence on the right. Note that in the intrinsic ventricular event (VS), the QRS complex is more narrow than after the paced event (QRS2). The marks on the left sides of these graphs 90, 91, would require the second method and the AP-VP to filter out the AR. While those at the right would require the first, or PVAB variance method to filter out the AR after the VP. Thus, to remove most false positive tachy detection indicators, both methods should be used together. Although one or the other method could by itself provide a significant improvement. FIG. 8 shows two AR events (95b and 95c) which would not be excluded even using both methods together, which would be most preferred, thus allowing for actual tachy detection. (A dotted line at 95a indicates a hidden AR event).

It will also be appreciated that the circuits described with reference to FIG. 2 are capable (as would be apparent to one of ordinary skill in this art) of carrying out software instructions and delivering pacing pulses in accord with these above described methods. Accordingly the invention is only considered limited as set forth in the following claims.

What is claimed is:

1. A method for operating an implantable pulse generator including the steps sensing atrial events and pacing in the atrium and the step:

determining whether atrial pacing is occurring, and if atrial pacing is occurring, not allowing a determination of atrial tachyarrhythmia to occur and if no atrial pacing is occurring, then allowing a determination of atrial tachyarrhythmia to occur.

2. A method as set forth in claim 1 wherein a further step is performed by which a determination of whether there is atrial tachyarrhythmia is made based on determining a current atrial interval (AAI/MAI) value, comparing said AAI/MAI value to a predetermined tachy value and further comprising the included step:

ignoring AP-AR intervals in determining said value for said current MAI.

3. A method as set forth in claim 1 wherein a further step is performed by which a determination of whether there is atrial tachyarrhythmia said determination being made based on determining a current atrial interval (AAI/MAI) value, comparing said current AAI/MAI value to a predetermined tachy value and further comprising the included steps:

sensing ventricular events, determining when a sequence of events is AP-AR-V, and removing the determination of the value of the AP-AR time interval from such sequences from the value of the current MAI AAI.

4. A method as set forth in claim 1 wherein determination of atrial tachyarrhythmia is made based on a step of comparing an atrial interval AAI/MAI value to a predetermined tachy value and further comprising the steps:

determining when a sequence of events is AP-AR-V, determining the value of MAI based only on those intervals that are not AP-AR intervals and only doing so after a predetermined period of time.

5. A method for operating an implantable pulse generator (IPG) including the steps sensing atrial events and pacing in the atrium and the step:

determining whether atrial pacing is occurring, and if atrial pacing is occurring, not allowing any antitachy or adaptive to tachy pacing operation(s) to be produced by said IPG.

6. A method for operating an implantable pulse generator including the step, sensing atrial events, and wherein the step:

a PVAB value is adjusted in said implantable pulse generator that after the occurrence of an atrial pace event the PVAB value is longer than after an atrial sense event.

7. A method as set forth in claim 6 which further includes the step of setting a value for a PVAB after a paced atrial event at approximately 200 ms and after an atrial sensed event at approximately 150 m sec.

8. An implantable pulse generator adapted to pace in the atrium of a living heart said IPG having means to determine whether atrial tachycardia or atrial flutter is occurring in said heart, and further comprising:

means for determining whether atrial pacing is occurring, means to override determination of atrial tachycardia if atrial pacing is occurring.

9. An implantable pulse generator adapted to pace in the atrium of a living heart said IPG having means to determine whether atrial tachycardia or atrial flutter is occurring in said heart, said means to determine having means to distinguish between AP and AR events and means for checking a value of a true atrial interval (MAI) and means for updating the value of said MAI based on the time between occurrence of atrial events, and further comprising:

means for determining whether atrial pacing is occurring, means to override determination of atrial tachycardia if atrial pacing is occurring.

10. An implantable pulse generator adapted to pace in the atrium of a living heart said IPG having means to determine whether atrial tachycardia or atrial flutter is occurring in said heart, said means to determine having means to distinguish between AP and AR events and means for checking whether a current value of a true atrial interval (MAI) is smaller than a predetermined tachy indication interval value, and means for updating the value of said MAI based on the time between occurrence of atrial events, and further comprising:

means for altering said means for updating said MAI such that said updated MAI does not include AP-AR interval values.

11. An implantable pulse generator adapted to pace in the atrium of a living heart said IPG having means to determine whether atrial tachycardia or atrial flutter is occurring in said heart, said means to determine having means to distinguish between AP and AR events and means for checking whether a current value of a true atrial interval (MAI) is smaller than a predetermined tachy indication interval value, means for updating the value of said MAI based on the time between occurrence of atrial events, and means for changing a PVAB length, and further comprising:

means for causing said PVAB length to be longer after an AP than after an AS.

* * * * *